US009162160B2

(12) United States Patent
Robinson et al.

(10) Patent No.: US 9,162,160 B2
(45) Date of Patent: *Oct. 20, 2015

(54) PROCESS FOR MAKING CRYSTALS

(75) Inventors: James Robinson, Oxfordshire (GB);
Graham Ruecroft, Oxfordshire (GB)

(73) Assignee: Prosonix Limited (GB)

( * ) Notice: Subject to any disclaimer, the term of this patent is extended or adjusted under 35 U.S.C. 154(b) by 286 days.

This patent is subject to a terminal disclaimer.

(21) Appl. No.: 12/531,322

(22) PCT Filed: Mar. 18, 2008

(86) PCT No.: PCT/GB2008/500191
§ 371 (c)(1),
(2), (4) Date: Sep. 15, 2009

(87) PCT Pub. No.: WO2008/114052
PCT Pub. Date: Sep. 25, 2008

(65) Prior Publication Data
US 2010/0018853 A1    Jan. 28, 2010

(30) Foreign Application Priority Data

Mar. 19, 2007 (GB) .................................. 0705159.2

(51) Int. Cl.
*B01J 19/10* (2006.01)
*B01D 9/00* (2006.01)

(52) U.S. Cl.
CPC ............ *B01D 9/0054* (2013.01); *B01D 9/0081* (2013.01); *B01J 19/10* (2013.01)

(58) Field of Classification Search
CPC .. B01D 9/0081; B01D 9/0054; B01D 9/0009; B01J 19/10; B01J 2/18; B01J 2/06; A61K 9/0073; A61K 9/14

USPC ...................................................... 204/157.62
See application file for complete search history.

(56) References Cited

U.S. PATENT DOCUMENTS

| 5,874,029 | A  | * | 2/1999  | Subramaniam et al. ......... 264/12 |
| 6,221,332 | B1 | * | 4/2001  | Thumm et al. ................ 422/131 |
| 6,302,958 | B1 | * | 10/2001 | Lindrud et al. ................. 117/65 |
| 6,482,438 | B1 |   | 11/2002 | Singh et al. |
| 6,960,256 | B2 | * | 11/2005 | Bowe et al. ................ 422/245.1 |

(Continued)

FOREIGN PATENT DOCUMENTS

| EP | 1688169      | 8/2006 |
| EP | 2360147 A1 * | 8/2011 |

(Continued)

OTHER PUBLICATIONS

PCT International Search Report and Written Opinion for International Application No. PCT/GB2008/050191 dated Aug. 4, 2008.

(Continued)

*Primary Examiner* — Keith Hendricks
*Assistant Examiner* — Colleen M Raphael
(74) *Attorney, Agent, or Firm* — Tumey L.L.P.

(57) ABSTRACT

A process for preparing crystalline particles of an active principal in the presence of ultrasonic irradiation that comprises contacting a solution of a solute in a solvent in a first flowing stream with an anti-solvent in a second flowing stream causing the mixing thereof, wherein the flow rate ratio of the anti-solvent: solvent is higher than 20:1, and collecting crystals that are generated.

8 Claims, 5 Drawing Sheets

(56) References Cited

U.S. PATENT DOCUMENTS

| | | | |
|---|---|---|---|
| 7,208,106 B2* | 4/2007 | Shekunov et al. | 264/5 |
| 7,326,294 B2* | 2/2008 | McCausland et al. | 117/70 |
| 2002/0000681 A1 | 1/2002 | Gupta et al. | |
| 2003/0181432 A1* | 9/2003 | Lancaster et al. | 514/175 |
| 2004/0045805 A1* | 3/2004 | Lancaster et al. | 204/157.43 |
| 2004/0091407 A1* | 5/2004 | Lancaster et al. | 422/245.1 |
| 2004/0197275 A1* | 10/2004 | Jongen et al. | 424/46 |
| 2004/0256749 A1* | 12/2004 | Chaubal et al. | 264/5 |
| 2004/0258756 A1 | 12/2004 | McLoughlin | |
| 2006/0150892 A1* | 7/2006 | Mayer | 117/2 |
| 2006/0182808 A1 | 8/2006 | Bakker et al. | |
| 2006/0255323 A1* | 11/2006 | Seki et al. | 252/519.21 |
| 2007/0065372 A1 | 3/2007 | Price et al. | |
| 2007/0082054 A1* | 4/2007 | Van Den Mooter et al. | 424/489 |
| 2009/0087492 A1* | 4/2009 | Johnson et al. | 424/489 |

FOREIGN PATENT DOCUMENTS

| | | |
|---|---|---|
| JP | WO 01/14036 | 3/2001 |
| JP | 2004-276334 | 10/2004 |
| WO | WO 0038811 | 7/2000 |
| WO | WO 0132125 | 5/2001 |
| WO | WO 03061816 | 7/2003 |
| WO | WO 03092851 | 11/2003 |
| WO | WO 2004062785 A1 * | 7/2004 |
| WO | WO 2006108572 | 10/2006 |

OTHER PUBLICATIONS

GB Search Report for Application No. GB0804995.9 dated Jul. 14, 2008.

USPTO Office Action for U.S. Appl. No. 12/665,019 dated Jul. 18, 2011.

USPTO Office Action for U.S. Appl. No. 12/665,019 dated Jan. 18, 2012.

Foreign Office Action for Canadian Application No. 2680105 CA dated Mar. 14, 2013.

English Translation of Foreign Office Action for Japanese Application No. 2009554087 dated Apr. 10, 2013.

Martin, Price, & Cains, "Sonochemistry and Sonoprocessing at Industrial Scale", The Third International Conference on the Scale-Up of Chemical Processes, dated Sep. 21, 1998.

Martin, Price, & Cains, "Sonochemistry", Process Technology, FCW, pp. 6-9, dated Dec. 1997.

Martin & Ward, "Reactor Design for Sonochemical Engineering", Trans I ChemE, vol. 70, Part A, May 1992, pp. 296-303.

* cited by examiner

Malvern laser defraction particle size analysis (Mastersizer 2000) was as follows:

D10  2.42  micron
D50  7.60  micron
D90  13.99 micron

MALVERN DATA d(0.1): 2.420 μm    d(0.5): 7.598 μm    d(0.9): 13.994 μm

Malvern laser defraction particle size analysis (Mastersizer 2000) was as follows:

D10  0.62  micron
D50  4.25  micron
D90  7.40  micron

PROCESS FOR MAKING CRYSTALS

FIELD OF THE INVENTION

This invention relates to a process for preparing small crystals. In particular, the invention relates to a process for preparing small crystals of a size of up to about 10 µm.

BACKGROUND OF THE INVENTION

The control of crystal and precipitate particle size is very important in some circumstances, in particular in the pharmaceutical and agro-chemical industries in which the final product form of the active principal of interest is in the form of a fine powder. The manner in which an active principal behaves in a biological system depends upon many factors inter alia the size of the particle and the crystal form. Small particles may be made by processes such as milling, but such processes may have a detrimental effect on the material properties and may also produce a significant proportion of particles which are unsuitable for the desired use, for example, they may be too small or of an inappropriate shape. Such particles may undergo morphological alterations, leading to undesirable surface polymorphological transformation which in turn may give rise to the formation of amorphous structures. The particles may become highly charged which may also contribute to undermining flow-rates. Also, particles destined for use in aerosols may be compromised should they become highly charged. Crystallisation of crystals in the desired size range directly from solution would be desirable.

For many years it has been known to bring about crystallisation by mixing a solvent containing an active principal to be crystallised with an anti-solvent, so that after mixing the solution is supersaturated and crystallisation occurs. The mixing may occur in the presence of ultrasonic irradiation or in a different manner in which ultrasonic irradiation is not used eg fluid vortex mixing. The term "anti-solvent" means a fluid which promotes precipitation from the solvent of the active principal of interest (or of a precursor of the active principal). The anti-solvent may comprise a cold gas, or a fluid which promotes the precipitation via a chemical reaction, or which decreases the solubility of the active principal of interest in the solvent; it may the same liquid as the solvent but at a different temperature, or it may be a different liquid from the solvent.

EP 1144065 describes a system in which mixing of anti-solvent with solvent comprising an active principal to be crystallised is achieved by using a flow rate ratio of anti-solvent: solvent of up to 10:1 in the presence of ultrasonic irradiation in a continuous flow cell. It is described that a warm solvent is mixed with a cold miscible anti-solvent, although the actual temperature of the cold anti-solvent is not disclosed.

EP 1469938 describes a system in which the flow rate of mixing of anti-solvent with solvent comprising an active principal to be crystallised exceeds that of the solvent, at a flow rate ratio of up to 10:1, typically of from 2:1 up to 5:1. The mixing is carried out in the presence of ultrasonic radiation.

The prior art processes enable the production of crystals using flow rate ratios of anti-solvent: solvent that are generally lower than 20:1 (i.e. towards a flow rate ratio of 10:1 to as low as 1:1).

SUMMARY OF THE INVENTION

According to the present invention there is provided a process for preparing crystalline particles of a substance in the presence of ultrasonic irradiation that comprises contacting at least one solute in a solvent in a first flowing stream with an anti-solvent in a second flowing stream wherein the flow rate ratio of the anti-solvent: solvent is higher than 20:1, and collecting crystals that are generated.

The anti-solvent stream is typically re-circulated, for example, in a continuously re-circulating flowing stream, that is to say, in a second flowing stream as described herein. Typically, there is provided a process according to the invention wherein the second flowing stream is a continuously recycling anti-solvent stream that can also comprise added solute in solvent, wherein the flow rate ratio of the said second flowing stream (ie anti-solvent): solvent is higher than 20:1.

By manipulating the flow rate ratio of anti-solvent to solvent in the process of the present invention the inventors have now made it possible to provide crystals of active principals of interest of a desired size of up to about 10 µm in size. The mean diameter size of particles that are able to be attained using the method of the invention lies in the range of from 500 nm up to 10 µm, preferably from about 600 nm to about 5 µm and most preferably from 650 nm to about 2 µm, for example, 700 nm or 1 µm.

The solute can be an active principal or a desired precursor thereof, such as a drug or an agro-chemical of interest that is able to form crystals in the process of the invention. There may be more than one solute comprised in the first flowing stream, for example, a mixture of two or more solutes of interest, such as two or more active principals of interest, for example, two or more drugs or two or more agro-chemicals, depending on the proposed end use of the said solutes. Suitable solutes that are able to crystallise under the process conditions of the invention include active principals or drugs which can be formed into crystalline particles by the process of the present invention such as corticosteroids, b2-agonists, anticholinergics, leukotriene antagonists, inhalable proteins or peptides, mometasone furoate; beclomethasone dipropionate; budesonide; fluticasone; dexamethasone; flunisolide; triamcinolone; salbutamol; albuterol; terbutaline; salmeterol; bitolterol; ipratropium bromide; oxitropium bromide; sodium cromoglycate; nedocromil sodium; zafirlukast; pranlukast; formoterol; eformoterol; bambuterol; fenoterol; clenbuterol; procaterol; broxaterol; (22R)-6a,9a-difluoro-11b, 21-dihydroxy-16a,17a-propylmethylenedioxy-4-pregnen-3, 20-dione; TA-2005; tipredane; insulin; interferons; calcitonins; parathyroid hormones; and granulocyte colony-stimulating factor.

Other particles which may be made according to the invention include any drugs or active principals usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone antitussives, e.g. noscapine; bronchodilators, e.g. ephedrine, adrenaline, fenoterol, formoterol, isoprenaline, metaproterenol, phenylephrine, phenylpropanolamime, pirbuterol, reproterol, rimiterol, salbutamol, salmeterol, terbutalin; isoetharine, tulobuterol, orciprenaline or (−)-4-amino-3,5-dichloro-a[[[6-[2-(2-yridinyl) ethoxy]hexyl]amino]methyl] benzenemethanol; diuretics, e.g. amiloride; anticholinergics e.g. ipratropium, atropine or oxitropium; hormones, e.g. cortisone, hydrocortisone or prednisolone; xanthines e.g. 25 aminophylline, choline theophyllinate, lysine theophyllinate or theophylline; and therapeutic proteins and peptides, e.g.

insulin or glucagon. It will be appreciated by the person skilled in the art that, where appropriate, medicaments comprising active principals or drugs may be used in the form of salts (e.g. as alkali metal or amine salts or as acid addition salts) or as esters (e.g. lower alkyl esters) or as solvates (e.g. hydrates) to optimise the activity and/or stability of the medicament.

Particularly suitable medicaments for preparation with particles obtained in accordance with the process of the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or as the sulphate salt), salmeterol (e.g. as the xinafoate salt), terbutaline (e.g. as the sulphate salt), reproterol (e.g. as the hydrochloride salt), beclomethasone dipropionate (e.g. as the monohydrate), fluticasone propionate or (−)-4-amino-3,5-dichloro-.alpha.-[[[6-[2-(2-pyridinyl)ethoxy]hexyl]amino]-methyl]benzenemethanol and physiologically acceptable salts and solvates thereof.

It will be appreciated by the man skilled in the art that particles made by the process of the invention may contain a combination of two or more active principals. Active principals may be selected from suitable combinations of the active principals mentioned hereinbefore. Thus, suitable combinations of bronchodilatory agents include ephedrine and theophylline, fenoterol and ipratropium, and isoetharine and phenylephrine.

Further suitable combinations of particles of active principals made according to the process of the invention include combinations of corticosteroids, such as budesonide, beclomethasone dipropionate and fluticasone propionate, with b2-agonists, such as salbutamol, terbutaline, salmeterol and fluticasone, salmeterol and formoterol and physiologically acceptable derivatives thereof, especially salts including sulphates.

Other examples of particles obtainable by the process of the invention may include a cromone which may be sodium cromoglycate or nedocromil, or may include carbohydrate, for example, heparin.

The particles made by the process of the invention may comprise an active principal suitable for inhalation and may be a pharmacologically active agent for systemic use. For example, such active particles may comprise peptides or polypeptides or proteins such as Dase, leukotines or insulin (including pro-insulins), cyclosporin, interleukins, cytokines, anticytokines and cytokine receptors, vaccines, growth hormone, leuprolide and related analogues, intereferons, desmopressin, immmunoglobulins, erythropoeitin and calcitonin.

Alternatively, the active principal made by the process of the invention may be suitable for oral administration. A drug for oral administration may be one of the systemic drugs mentioned above. The active principal may be a substance which exhibits low solubility in the digestive tract, for example, magnesium trisilicate, calcium carbonate and bismuth subnitrate. Organic compounds may include, for example, all products of combinatorial chemistry, rosiglitazone and other related glitazone drugs, hydrochlorothiazide, griseofulvin, lamivudine and other nuclease reverse transciptase inhibitors, simvastatin and other statin drugs, benzafibrate and other fibrate drugs and loratidine, and any other physiologically tolerable salts and derivatives thereof.

Pharmaceutical excipients suitable for adding to particles made according to the process of the invention include, for example, carbohydrates especially monosaccharides such as fructose, glucose and galactose; non-reducing disaccharides such as sucrose, lactose and trehalose; non-reducing oligosaccharides such as raffinose and melezitose; non reducing starch derived polysaccharides products such as maltodextrins, dextrans and cyclodextrins; and non-reducing alditols such as mannitol and xylitol.

Where the particles of active principal(s) prepared by the process of the present invention are agro-chemically active, the active principal may for example be a plant growth regulator, herbicide, and/or pesticide, for example insecticide, fungicide, acaricide, nematocide, miticide, rodenticide, bactericide, molluscicide or bird repellant.

Examples of organic water-insoluble agrochemical active principals made according to the process of the invention include insecticides, for example selected from the group consisting of carbamates, such as methomyl, carbaryl, carbofuran, or aldicarb; organo thiophosphates such as EPN, isofenphos, isoxathion, chlorpyrifos, or chlormephos; organo phosphates such as terbufos, monocrotophos, or terachlorvinphos; perchlorinated organics such as methoxychlor; synthetic pyrethroids such as fenvalerate; nematicide carbamates, such as oxamyl herbicides, for example selected from the group consisting of triazines such as metribuzin, hexaxinone, or atrazine; sulfonylureas such as 2-chloro-N-[(4-methoxy-6-methyl-1,3,5-triazin-2-yl)aminocarbonyl]-benzenesulfonamide; uracils (pyrimidines) such as lenacil, bromacil, or terbacil; ureas such as linuron, diuron, siduron, or neburon; acetanilides such as alachlor, or metolachlor; thiocarbamates such as benthiocarb (SATURN), triallate; oxadiazol-ones such as oxadiazon; phenoxyacetic acids such as 2,4-D; diphenyl ethers such as fluazifop-butyl, acifluorfen, bifenox, or oxyfluorfen; dinitro anilines such as trifluralin; glycine phosphonates such as glyphosate salts and esters; dihalobenzonitriles such as bromoxynil, or ioxynil; fungicides, for example selected from the group consisting of nitrilo oximes such as cymoxanil (curzate); imidazoles such as benomyl, carbendazim, or thiophanate-methyl; triazoles such as triadimefon; sulfenamides such as captan; dithiocarbamates such as maneb, mancozeb, or thiram; chlorinated aromatics such as chloroneb; dichloro anilines such as iprodione; aphicides, for example selected in the group consisting of carbamates, such as pirimicarb; miticides, for example selected from the group consisting of propynyl sulfites such as propargite; triazapentadienes such as amitraz; chlorinated aromatics such as chlorobenzilate, or tetradifan; and dinitrophenols such as binapacryl.

The organic water-insoluble agrochemical active principals may be comprised in the particles produced according to the present invention as a mixture of several ingredients. Especially preferred organic water-insoluble agrochemical active ingredients are atrazine, cymoxanil, chlorothalanil, cyproconazole, and tebuconazole.

The flowing stream of solvent comprising solute (i.e. the 'solution') and the flowing stream of anti-solvent may be contacted or mixed together such that the two streams flow along a single path or axis in the same direction, for example, within the lumen of a suitable delivery means and into a suitable receptacle or chamber, such as an ultrasonic continuous flow cell. Each of the said flowing streams may be pumped at a pre-determined rate of flow from an initial source reservoir into the delivery means. A suitable delivery means may comprise a tubular means such as a straight or curved conduit, for example a pipe, and the two streams may be mixed coaxially therein. Alternatively, the two streams may be introduced into a receptacle or chamber, such as an ultrasonic continuous flow cell, via pumping through separate delivery means, such as two separate tubular means, for example, two pipes.

The flow rate ratio of anti-solvent: solvent (the "flow rate ratio" hereinafter) of the invention is higher than 20:1, and may be of any flow rate ratio depending on design and the end purpose for the crystals that are obtained using the process of the invention. The flow rate ratio employed in the process of the invention may be decided taking into account the substance of interest, the desired size of the crystals required for a given purpose, and how the crystals are to be administered to a subject, such as to a mammal (e.g. a human being; a horse; a bovine animal; or a sheep) in the form of a suitable medicament, or to a plant in the form of a suitable agrochemical, for example a pesticide, a herbicide, a fungicide, bactericide, or a virucide. Suitable flow rate ratios for use in the process of the invention may be any flow rate ratio of the second flowing stream:first flowing stream, up to 1000:1, for example, 900:1, 800:1, 700:1, 600:1, 500:1, 400:1, 300:1, 200:1, 100:1, 50:1, 40:1, or 30:1 or any flow rate ratio there between, such as 380:1, 330:1, 333:1, 165:1, 80:1 and the like. The flow rate ratio will be governed by the size of the crystals that are required for a given end purpose and the proposed delivery vehicle for them that is to be used in a subject organism.

Typically, the flow rate of the anti-solvent stream through an apparatus suitable for producing crystalline particles using the process of the invention is in the range of liters per hour (l/hr) [e.g. 20 L/hr] rather than milliliters per hour (ml/hr) and may be any flow rate suitable for the end purpose in question so long as the flow rate of the anti-solvent is higher than that of the solvent system (ie solute in solvent) by a factor of at least 20:1 and higher as herein defined. For example, the flow rate for the first stream flow of the invention may be 20 l/hr and that of the second stream flow 60 ml/hr for a bench top apparatus. Where the process is employed in a larger apparatus, for example, a 100 liter (100 l) vessel the throughput flow rates for the first stream may be 2400 l/hr and for the second stream 120 l/hr. Naturally, the man skilled in the art will appreciate that the rate of flow for each of the said streams can be at any desired rate of flow provided that the flow rate ratio of the two streams is that described for the present invention The flow rate of the anti-solvent, in a small scale apparatus, such as one having a 1 liter capacity, 5 liter or 10 liter capacity, may be up to 50 l/hr, typically up to 40 l/hr, 30 l/hr, 20 l/hr 10 l/hr or 5 l/hr or of any value in between, such as 4 l/hr, 8 l/hr, 15 l/hr and so on. The flow rate may be decided upon by the skilled addressee depending on the size of particles required for a chosen administration route to a site of interest for a particular end purpose. Correspondingly, the flow rate of the added solution of solute in solvent will be at least 20 times less than that of the anti-solvent with which it is to be placed in contact. An example of a flow rate ratio (333:1) used in the present invention is to be found in the examples wherein the anti-solvent flows at 20 l/hr and the solute in solvent at 60 ml/hr.

It will be appreciated that the anti-solvent and the solvent should be selected as being suitable for a particular active principal or active precursor thereof. The anti-solvent and solvent pair may be miscible with each other. Examples of miscible pairs include water and 2-propanol; and ethanol and water. Alternatively, the anti-solvent and solvent pair may be the same liquid but at different temperatures. Typically, the temperatures of the liquid may lie between −10° C. and +120° C., but with a substantial temperature difference between the two. The temperatures may be separated by a temperature difference of 50° C. or more, for example, where the solvent is hot water (e.g. 80° C.) and the anti-solvent is cold water (e.g. 10° C.). The selection of appropriate solvent and anti-solvent must be made in accordance with the substance to be crystallised.

Once inside the receptacle, for example a continuous ultrasonic flow cell, the combined streams of anti-solvent and solvent are subjected to ultrasonic irradiation to form crystals of a desired mean size. The ultrasonic energy induces nucleation and subsequent crystallisation of the solute in the anti-solvent in the operating vicinity of the ultrasonic probe if used, or of an ultrasonic energy transducer, such as a wrap-around ultrasonic energy transducer, if such a configuration is employed. The ultrasonic energy may be applied continuously or in a discontinuous manner, such as by pulsed application. Any suitable source of ultrasonic irradiation may be used. An ultrasonic probe may, for example, be inserted into a mixing vessel, such as a continuous ultrasonic flow cell, an ultrasonic emitter may be contained in the mixing vessel, or the mixing vessel may be housed in an ultrasonic bath or it may have an ultrasound transducer fixed to the external walls of the mixing vessel. The amplitude and frequency of the ultrasound waves affects the rate of nucleation and crystal growth. The frequency of the ultrasound waves may for example be from 20 kHz to 1 MHz, preferably from 10-500 kHz, more preferably from 10-100 kHz such as at 10, 20, 40, 60, 80, or 100 kHz or at any frequency thereinbetween, such as, 20 kHz or 40 kHz.

The ultrasonic irradiation is employed at an amplitude that is appropriate for the formation of crystals of the desired size, for a pre-determined application. For laboratory probe systems with an emitting face of for example, 80 $cm^2$, the amplitude selected may be from about 1-30 µm, typically from 3-20 µm, preferably from 5-10 µm, for example, 5 µm. Probes having a probe face surface area of 8 $cm^2$ and a power requirement of from 5-80 W, provide a power density of from 0.6-12.5 $W/cm^2$ using an amplitude of 2-15 micron. In larger systems, comprising transducers bonded onto the flow cell, for example a 6 liter flow cell, the power density for the transducers employed may be from 150-600 W/l, preferably from 250-600 W/l, and more preferably from 300-600 W/l, for example 250 W/l or 450 W/l.

The residence time of the mixed components in the ultrasonic flow cell may be from 10 ms up to about 10 s. For re-circulation systems the residence time can be longer depending on design. The skilled addressee will appreciate that the residence time in the ultrasonic flow cell for each volume of fluid that is placed in it will be of the order of 10 ms up to 10 s, depending on design.

The process may be employed in reactors employed in the art such as in a batch fed reactor or in a continuous flow reactor, depending on design. The man skilled in the art is well acquainted with such reactor types and their operation. Generated crystals may be gathered or harvested from the batch chamber by drawing off crystals using conventional means in the art, such as by the process described in WO 03/092851.

The invention will now be described with reference to the accompanying examples and figures. It is to be understood that the examples and figures are not to be construed as limiting the scope of the invention in any manner.

DETAILED DESCRIPTION OF THE INVENTION

The process of the invention may be carried out using conventional equipment as shown in the accompanying figures in which.

Figure 3:
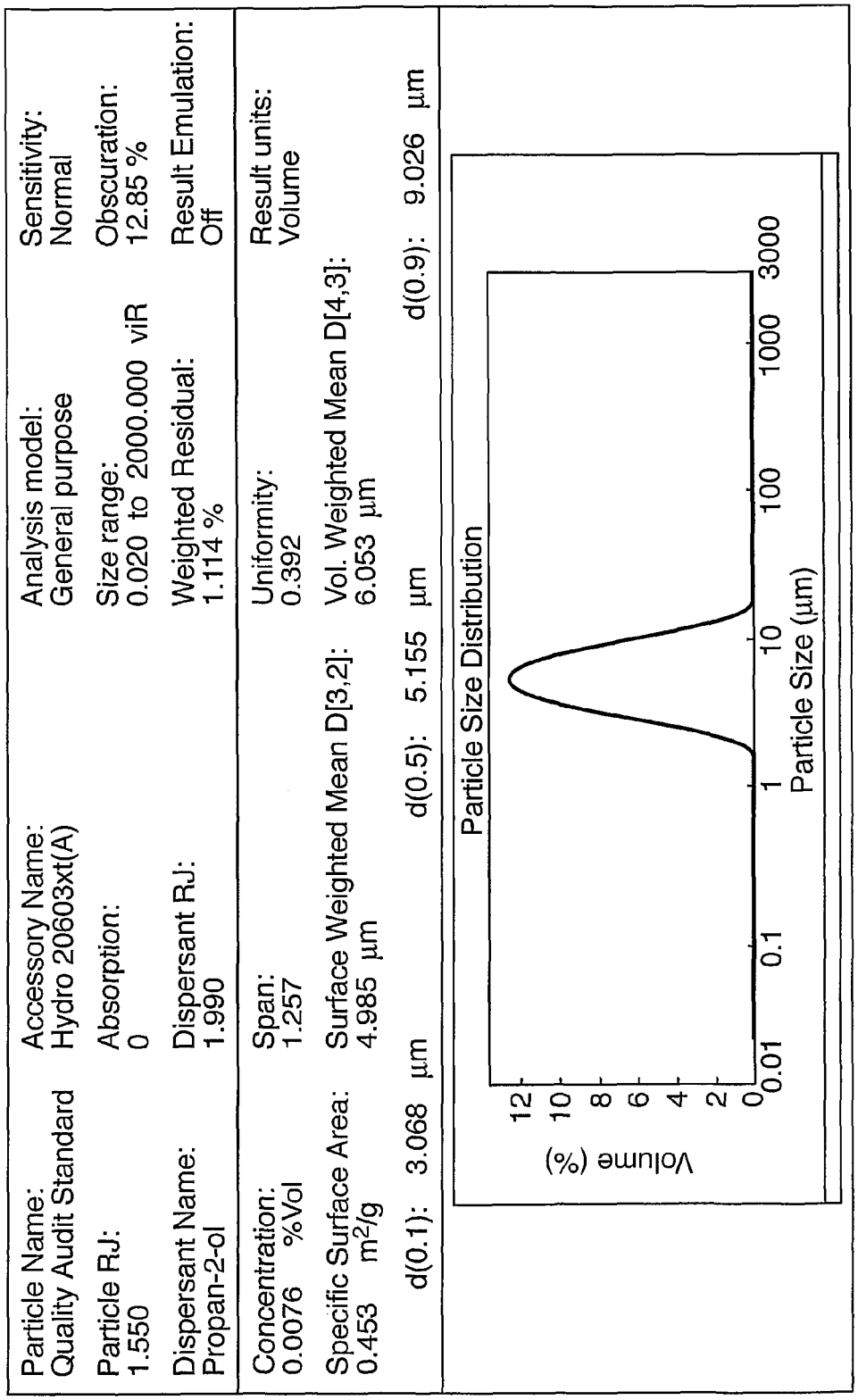
Figure 4:
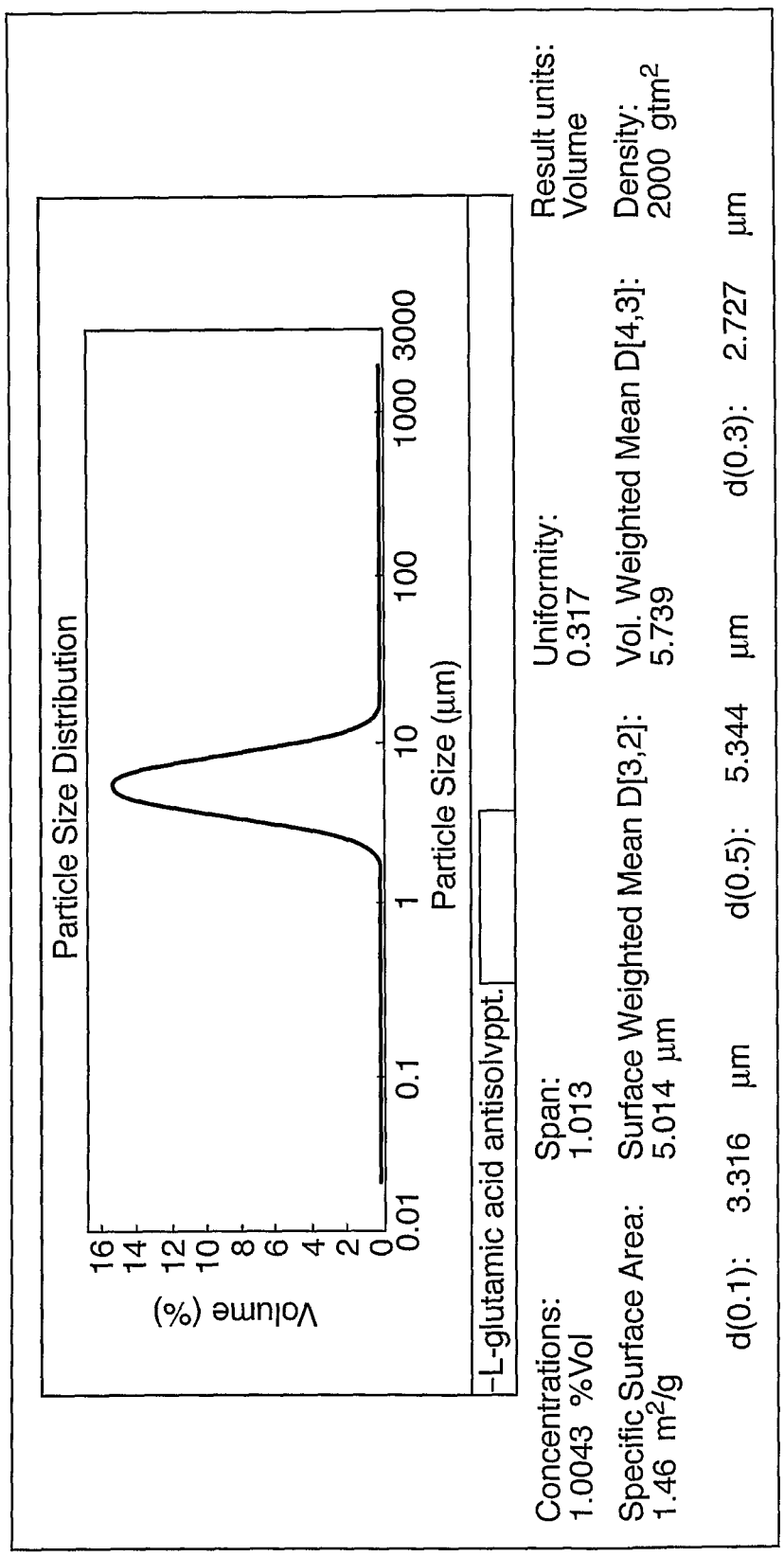
Figure 5:
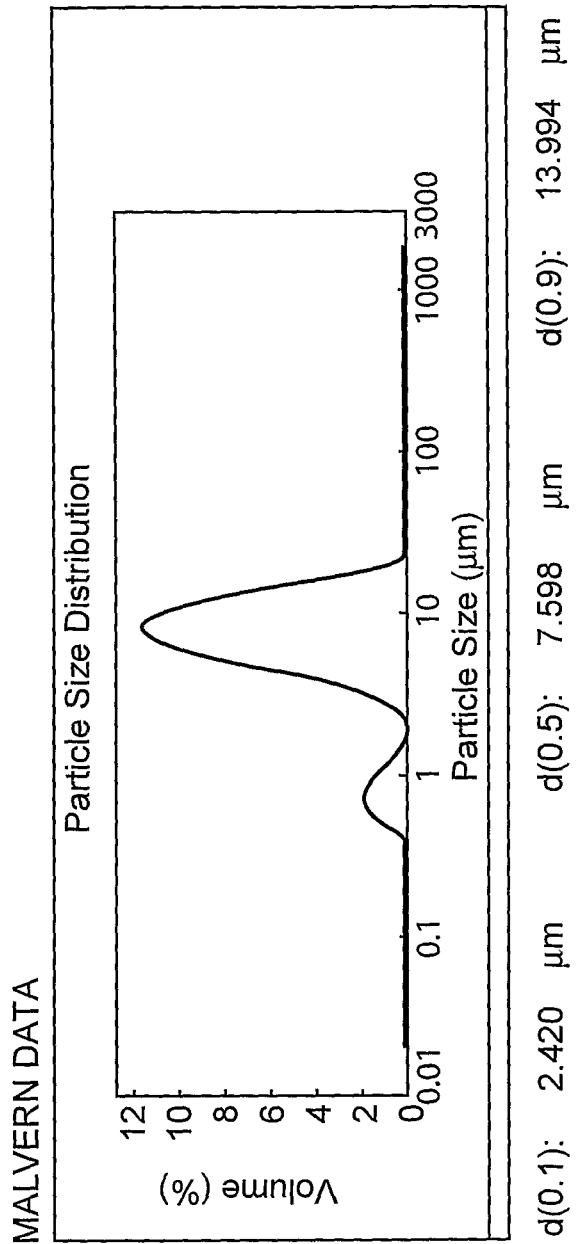
Figure 6:
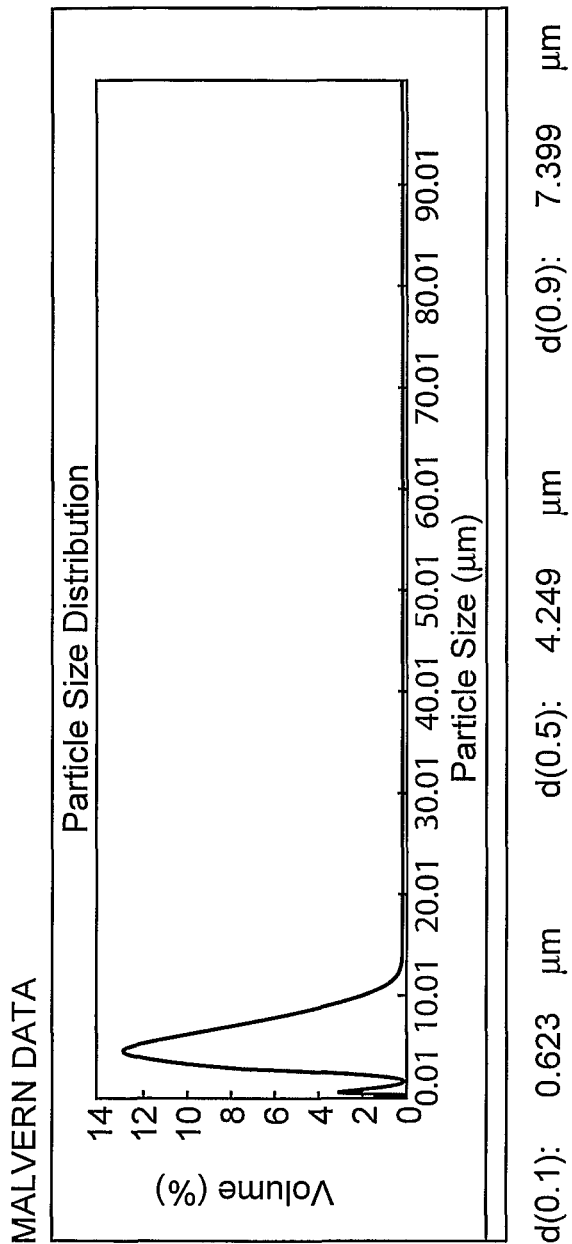

FIG. 3 shows the results for Example 1.
FIG. 4 shows the results for Example 2.
FIG. 5 shows the results for Example 3.
FIG. 6 shows the results for Example 4.

Figure 1:
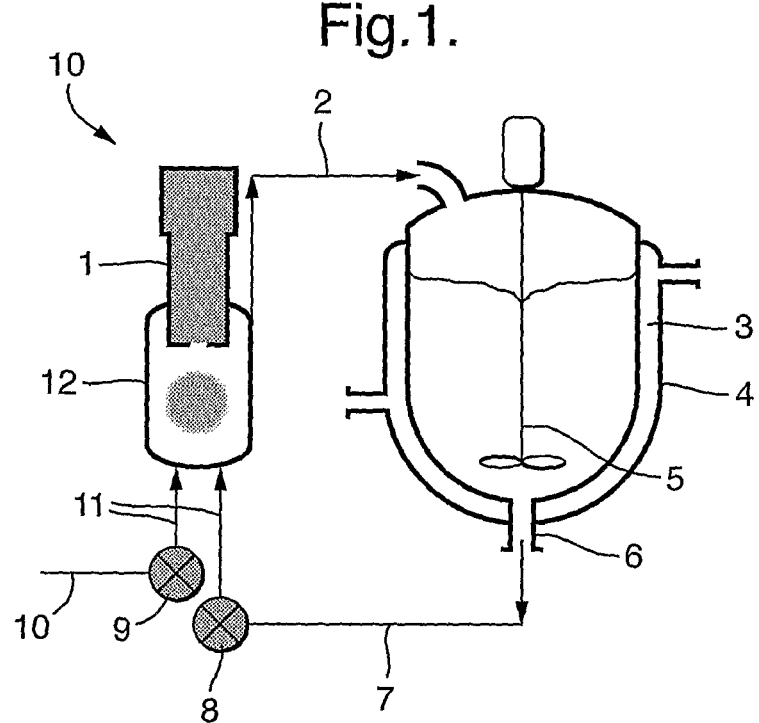
FIG. 1 shows a longitudinal sectional view of a crystallisation apparatus incorporating two separate feed stream delivery means for the solvent and anti-solvent leading into an ultrasonic continuous flow cell having an ultrasonic probe placed therein.

Turning to FIG. 1, closed loop crystallisation apparatus 10 comprises an impeller 5 in a first feed chamber 4 (surrounded by a thermal jacket 3), with an axial outlet 6 through which liquid anti-solvent flows into a delivery means 7 and is pumped at a first flow rate via pump 8 into an ultrasonic flow cell chamber 12. Concurrently, a liquid solute in solvent is pumped via a pump 9 at a flow rate different from that of the anti-solvent from a second chamber (not shown) via delivery means 10 through to delivery means 11 and into ultrasonic flow cell chamber 12 where the two liquids are mixed. Ultrasonic probe 1 irradiates the mixture with ultrasonic energy and the mixture flows through an outlet 2 and into the first feed chamber 4, completing a continuous closed flow loop. The flow cycle is repeated until crystallised particles of a desired size are attained. Thus in use of the apparatus 10, the saturated solution is thoroughly and rapidly mixed with the anti-solvent, the volume of the chamber 4 and the flow rates being such that the residence time in the ultrasonic flow cell chamber 12 is for example, 10 s. The ultrasonic energy from the probe 1 insonates the entire volume of the chamber 12 with sufficient intensity to cause dispersion and nucleation, as localised cavitation occurring on a microscopic scale promotes changes in fluid temperature and pressure that induce nucleation (and also promotes formation of the stable polymorph). By adjusting the power of the ultrasound, and the residence time in chamber 12, the degree of nucleation can therefore be controlled. The ultrasound has the additional benefit that any crystal deposits within the chamber 12 tend to be removed from the surfaces.

The skilled addressee will appreciate that the closed loop crystallisation apparatus 10 of FIG. 1 may be configured differently, for example, by replacing delivery means 11 with a single delivery means wherein the two liquid feeds from delivery means 7 and 10 may be contacted coaxially therein, prior to being fed into ultrasonic flow cell chamber 12 through a single inlet.

Figure 2:
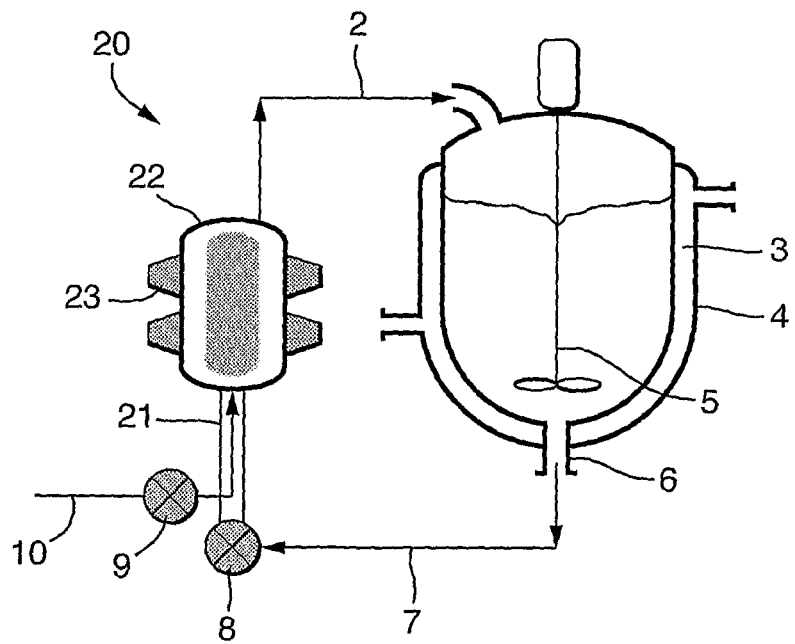
FIG. 2 shows a longitudinal sectional view of a crystallisation apparatus incorporating a single feed stream delivery means where the solvent and anti-solvent are introduced coaxially, mixed, and driven in a single stream into an ultrasonic continuous flow cell having an ultrasonic transducing apparatus bonded onto it.

Referring to FIG. 2, closed loop crystallisation apparatus 20 is of a similar configuration to that of FIG. 1 except that chamber 22 has a wrap-around ultrasonic transducer 23 located on the external surface of it. The wrap-around transducer 23 insonates the entire volume of the chamber 22 with sufficient intensity to cause nucleation and by adjusting the power of the ultrasound, and the residence time in the chamber 22, the degree of nucleation can therefore be controlled. The ultrasound has the additional benefit that any crystal deposits within the chamber 22 tend to be removed from the surfaces.

A further difference of the configuration of FIG. 2 from that of FIG. 1 is that the two liquid feeds from delivery means 7 and 10 are contacted coaxially within a single delivery means 21 and fed into the ultrasonic chamber 22 via a single inlet.

The skilled addressee will again appreciate that the delivery means to the ultrasonic flow chamber 22 could also follow the configuration of that of FIG. 1.

The skilled addressee will appreciate that the thermal jacket is designed to help maintain the temperature of the anti-solvent at a desired temperature, depending on design.

Example 1

2-Propanol (0.7 L) was charged to a 1 L stirred crystallizer (200 rpm) fitted with a thermo-regulation jacket. The temperature was adjusted to 16° C. The 2-propanol was pumped around a recirculation loop using a diaphragm pump (operating at 20 l/h) and a 60 ml thermo-regulated glass ultrasonic flow-cell fitted with a 30 mm diameter 20 kHz ultrasonic probe. The probe was held at the highest position in the flow-cell and sealed/clamped at a point of zero vibration (node point). The flow-cell was thermo-regulated at 16° C. Continuous ultrasound was applied at 15 W power, 5 µm amplitude. L-Valine (1.5 g) was dissolved in water (35 ml) and then pumped into the ultrasonic flow-cell using a second inlet on the underside of the flow-cell at a rate of 60 ml/h. Upon complete addition of the L-valine solution the microcrystalline product was isolated by micro-filtration or spray drying.

Results are shown in FIG. 3.

Example 2

2-Propanol (1 L) was charged to a 1 L stirred crystallizer fitted with thermo-regulation jacket. The temperature was adjusted to 16° C. The 2-propanol was pumped around a recirculation loop using a diaphragm pump (operating at 20 l/h) and a 60 ml thermo-regulated glass ultrasonic flow-cell fitted with a 30 mm diameter 20 kHz ultrasonic probe. The probe was held at the highest position in the flow-cell and sealed/clamped at a point of zero vibration (node point). The flow-cell was thermo-regulated at 16° C. Continuous ultrasound was applied at 15 W power, 5 µm amplitude. L-glutamic acid (4.5 g) was dissolved in water (100 ml) to form a saturated solution and then pumped into the ultrasonic flow-cell using a second inlet on the underside of the flow-cell at a rate of 60 ml/h. Upon complete addition of the L-glutamate solution the microcrystalline product was isolated by micro-filtration or spray drying.

Results are shown in FIG. 4.

Example 3

Heptane (0.75 L) was charged to a 1 L stirred crystallizer (250 rpm) fitted with a thermo-regulation jacket. The temperature was adjusted to 5° C. The heptane was pumped around a recirculation loop using a diaphragm pump (operating at 20 L/h) and a 60 ml thermo-regulated glass ultrasonic flow-cell fitted with a 30 mm diameter 20 kHz ultrasonic probe. The probe was held at the highest position in the flow-cell and sealed/clamped at a point of zero vibration (node point). The flow-cell was thermo-regulated at 5° C. Continuous ultrasound was applied at 15 W power, 5 micron amplitude. Budesonide (1.5 g) was dissolved in methanol (100 mL) and then pumped into the ultrasonic flow-cell using a second inlet on the underside of the flow-cell at a rate of 20 mL/h. Upon complete addition of the budesonide solution, the mixture was kept under recirculation for further 30 minutes. The microcrystalline product was isolated by either supercritical carbon dioxide assisted drying (to remove non-polar solvents), micro-filtration or spray drying.

Results are shown in FIG. 5.

Example 4

Water (0.7 L) was charged to a 1 L stirred crystallizer (200 rpm) fitted with a thermo-regulation jacket. The temperature was adjusted to 16° C. The water was pumped around a recirculation loop using a diaphragm pump (operating at 20 l/h) and a 60 ml thermo-regulated glass ultrasonic flow-cell fitted with a 30 mm diameter 20 kHz ultrasonic probe. The probe was held at the highest position in the flow-cell and sealed/clamped at a point of zero vibration (node point). The flow-cell was thermo-regulated at 16° C. Continuous ultrasound was applied at 15 W power, 5 micron amplitude. Olmesartan (2.1 g) was dissolved in butanone (70 mL) and then pumped into the ultrasonic flow-cell using a second inlet on the underside of the flow-cell at a rate of 20 mL/h. Upon complete addition of the olmesartan solution the microcrystalline product was isolated by micro-filtration or spray drying.

Results are shown in FIG. 6.

What is claimed:

1. A process for preparing crystalline particles of at least one active principal suitable for inhalation therapy in the presence of ultrasonic irradiation that comprises adding, in an ultrasonic flow cell forming part of a closed flow loop, a solution of at least one solute in a solvent in a first flowing stream into an anti-solvent in a second flowing stream causing the mixing and contacting thereof, wherein the flow rate ratio of the anti-solvent: solvent is higher than 20:1, the ultrasonic irradiation inducing nucleation and so crystallization of the at least one solute, and, during addition of the solution, recirculating the anti-solvent stream with the added solvent, with at least one solute and the resultant crystalline particles as a continuously recirculating stream around the closed flow loop and through the ultrasonic flow cell, wherein there is a pre-set volume of the anti-solvent in the closed flow loop, and the volume of the anti-solvent and the flow rate of the anti-solvent are selected such that, during the period of addition of the solution, the anti-solvent is recirculated multiple times around the closed flow loop, and subsequently collecting the crystalline particles that are generated.

2. A process according to claim 1 wherein the liquid anti-solvent is miscible with the liquid solvent.

3. A process according to claim 1 wherein the flow rate ratio of anti-solvent: solvent is up to 1000:1.

4. A process according to claim 1 wherein the solute comprises a mixture of two active principals.

5. A process according to claim 1 wherein the at least one active principal is fluticasone propionate.

6. A process according to claim 1 wherein the at least one active principal is salbutamol.

7. A process according to claim 1 in which the anti-solvent and solvent are the same liquid and the anti-solvent is held at a different temperature to that of the solvent.

8. A process according to claim 1 wherein the temperatures of the anti-solvent and solvent lie between −10° C. and +120° C. and the temperatures of the solvent and anti-solvent are separated by a temperature difference of at least 50° C.

* * * * *